Figure 3:
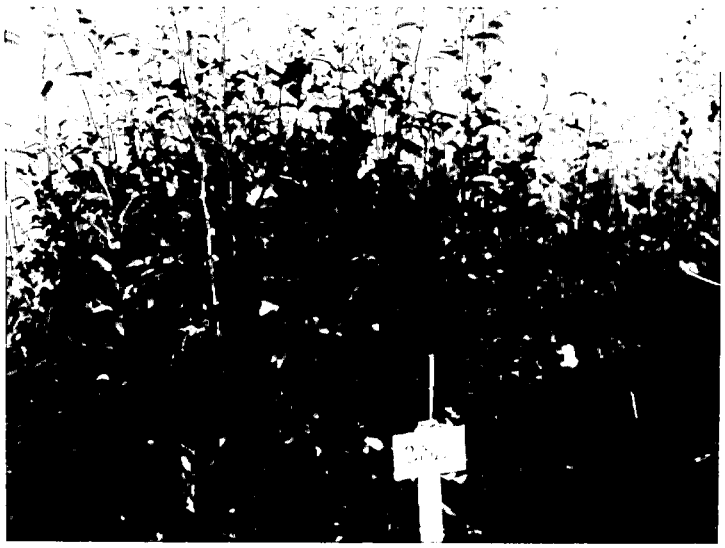
Figure 4:
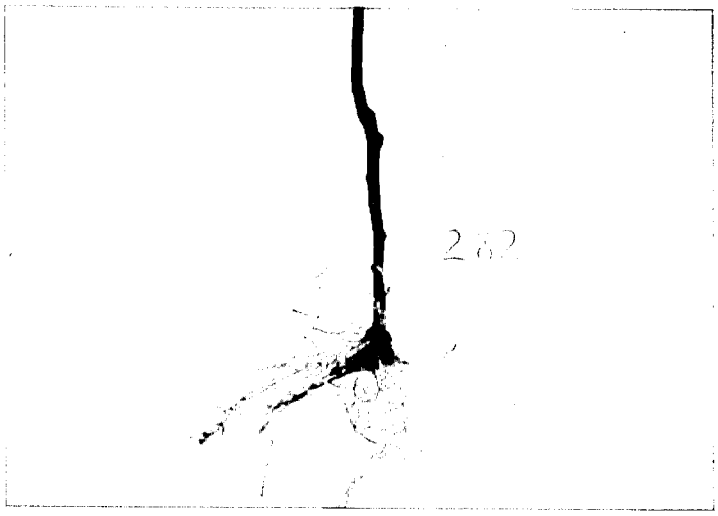

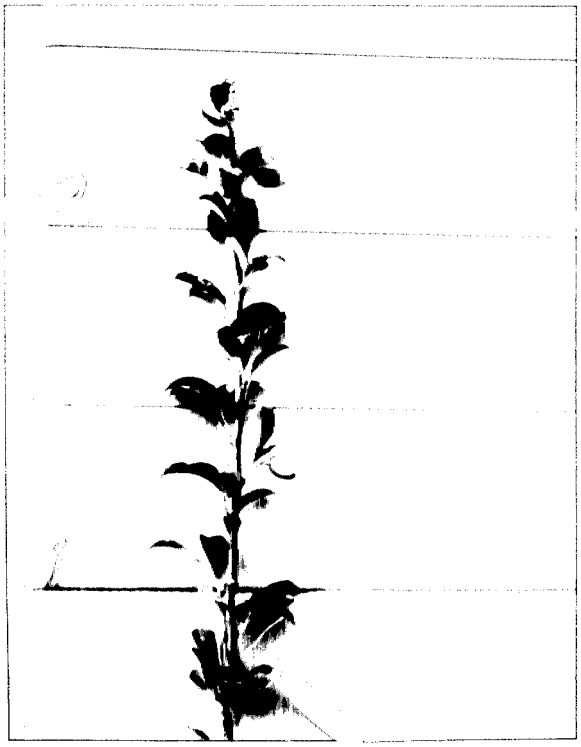
FIG. 1
FIG. 2
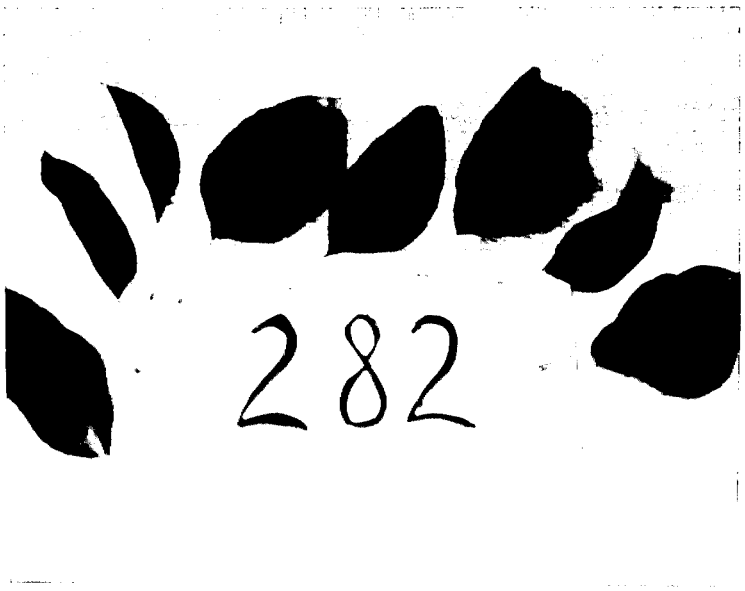

United States Patent [19]

Brooks

[11] Patent Number: Plant 5,573

[45] Date of Patent: Oct. 15, 1985

[54] PEAR TREE

[75] Inventor: Lyle A. Brooks, Forest Grove, Oreg.

[73] Assignee: Carlton Nursery Company, Inc., Dayton, Oreg.

[21] Appl. No.: 534,178

[22] Filed: Sep. 20, 1983

[51] Int. Cl.[4] ..... A01H 5/03

[52] U.S. Cl. ..... Plt./36

[58] Field of Search ..... Plt./36

*Primary Examiner*—Robert E. Bagwill

*Attorney, Agent, or Firm*—Harvey B. Jacobson

[57] ABSTRACT

This invention relates to a new and distinct variety of pear tree (Variety 282) which is useful as a size-controlling clonal pear rootstock. The new variety originated as a single seedling which was selected from a large group of pear seedlings which were grown from open-pollinated seed. This seed was harvested from Old Home pear trees (*Pyrus communis*) growing in an isolated planting with Farmingdale pollinizers.

Pear varieties grown on the understock of this new rootstock clone are "standard" in size when planted and grown in the orchard and are of like size to trees propagated on Domestic Bartlett seedling rootstocks (*Pyrus communis*). This new rootstock selection can be easily increased by vegetative means; particularly by hard and softwood cuttings. It is graft-compatible with all major pear varieties. It was selected for its non-rootsuckering habit, its resistance to the Fireblight disease and its tolerance of the Pear Decline disease. It is hardy, early-bearing and well-anchored in the orchard and in the nursery.

4 Drawing Figures

SUMMARY OF THE INVENTION

The original plant of this new variety was a member of a family of over 2000 pear seedlings which germinated from seed obtained from the Canadian Department of Agriculture Research Unit located near Summerland, British Columbia, Canada. This seed, collected from open-pollinated Old Home pear trees (*Pyrus communis*) which were growing in an isolated experimental planting with Farmingdale pollinizers, was planted by the inventor in his nursery at Forest Grove, Oreg. in 1952.

Experimental objectives were to develop, by trial and selection, a series of clonal pear rootstocks which would fulfill several urgent needs of both the orchardist and the nurseryman. The most important and immediate needs were for rootstocks that are resistant to Fireblight (*Erwinia amylovora*) a common, debilitating bacterial disease of pear trees. Also needed were rootstocks that are tolerant of the more recently described and equally destructive disease of pear known as Pear Decline which is a virus-like, mycoplasma-caused disorder affecting pear phloem sieve tubes below the graft union.

Another experimental objective was to select from this seedling population, rootstock clones which would root readily by vegative means. The most major additional objective was to determine and select a series of growth-controlling rootstock clones which would permit orchardists to develop plantings using tree spacing techniques tailored to known uniform tree sizes.

Old Home × Farmingdale #282 has shown its usefulness by exhibiting the following characteristics which fulfill all of the original desired objectives. It has been chosen as the best of several "standard" size-controlling selections after nearly 30 years of orchard and nursery testing and evaluation.

Final selection was made in 1982 following tests which consisted of trial plantings and nursery evaluations which were carried out at Geneva, N.Y.; and Hood River, Salem, Medford, Corvallis, Dayton and Forest Grove, Oreg.

TEST AND EVALUATION RESULTS

1. Pear trees grown on the rootstock of this variety develop into "standard" size trees in the orchard. This determination was made by comparing them to like trees growing on the most commonly used commercial pear rootstocks used in the trade which are seedling rootstocks grown from Domestic Bartlett seed and also known as Domestic pear seedlings (*Pyrus communis*). Trees grown on Bartlett seedling rootstocks are considered "standard" in size when established in the orchard and are used as the basis for all of our comparisons and measurements herein.

2. Rootstocks of this new variety are almost completely resistant to Fireblight infection whereas Domestic Bartlett seedling rootstocks have been shown to be highly susceptible.

3. This new clonal pear rootstock has shown itself to be Pear Decline tolerant. No Pear Decline symptoms were recorded on trees grafted to this rootstock through the many years of testing and evaluation in the several plots where tests were conducted. In comparison, decline symptoms were noted on trees grafted to Domestic Bartlett seedlings as well as on trees grafted to several other seedling rootstock types being evaluated.

4. Our new pear rootstock clone has been virus-indexed and found to be free of all known virus diseases of pear.

5. Less than one percent of the trees grafted on this stock showed signs of root-suckering; by comparison, Bartlett seedling rootstocks showed about three percent of trees with root-suckers.

6. Yield efficency has been about equal to trees on Bartlett seedling rootstocks. Yield efficency was determined by comparing yield to unit of tree size.

7. Young Bartlett trees propagated on this new rootstock variety showed a slight tendency to come into bearing at an earlier age than similar trees grafted on Domestic seedling stocks. About forty percent of the Bartlett trees grafted to Old Home × Farmingdale

#282 were producing some fruit in the third year in the orchard whereas only a few Bartlett trees grafted on seedling stocks were producing fruit in their fourth growing season.

8. This rootstock selection is hardy in all areas where it was tested and is considered to be hardy wherever pears are grown.

9. The new rootstock is graft-compatible with all major commercially grown pear varieties.

10. Pear trees grown on this selection show good root-anchorage in the nursery and in the orchard.

11. Pear rootstock trees of the Old Home × Farmingdale #282 variety can be easily propagated by hardwood and softwood cuttings and/or by micropropagation methods (meristematic tissue culture). Such asexual reproductions have demonstrated that its distinctive characteristics including its growth controlling "standard" tree size character are stable and are transmitted without change through succeeding propagations and generations.

GENERAL AND DETAILED DESCRIPTION

Since Old Home × Farmingdale #282 is a variety intended to be used only as a rootstock for pear cultivars, the main detailed description and accompanying drawings will center on the vegetative parts rather than the flowers and fruits. This pear selection will be propagated only asexually rather than by seed, in order to maintain its clone characteristics. The accompanying pictures show typical specimens of this new clonal pear rootstock.

FIG. 1

This picture shows a one-year old shoot of Old Home × Farmingdale #282 taken from the cuttingbed showing its straight, upright and branchless habit growth.

FIG. 2

This picture shows typical leaves of Old Home × Farmingdale #282 showing its broad-ovate shape and medium length, thin petioles; also showing its very small, narrow stipules at the base.

FIG. 3

This picture shows typical growth of Old Home × Farmingdale #282 in the nursery cuttingbed.

FIG. 4

This picture shows a rooted hardwood cutting of Old Home × Farmingdale #282 taken from the cuttingbed showing typical root development at the basal cut.

DESCRIPTION OF VEGETATIVE CHARACTERISTICS

The following is a detailed description of the new pear rootstock's growth characteristics as observed on one year old shoots produced from hardwood cuttings which were grown in a cuttingbed located in the propagation nursery at Forest Grove, Oreg. These observations were made during the late growing season after vigorous spring and summer growth had ceased but prior to fall leaf senescence. The new variety was also observed closely outdoors in the late fall during digging operations and again later in our a tree storage warehouse where all stocks were evaluated for rooting characters prior to grading and storage. The characteristics described are those most often seen and used in the identification of a clonally propagated rootstock.

Colors of leaves and shoots herein described are based on their appearance at the site where stocks were grown, dug and stored. In those instances where a precise color assessment can be made reference is to a Munsell Limit Color Cascade chart. In other instances, general color terms are used in accordance with their ordinary dictionary significance.

General habit:
- *Strength of growth.*—Vigorous, flexible, slender.
- *Habit.*—Uright.
- *Branching.*—Thin, flexible, almost branchless.

Wood-Summer:
- *Color.*—Brownish-green (23-11) on upper side, dark-green (22-12) on lower side.
- *Pubescence.*—None.
- *Texture.*—Smooth.

Wood-Winter:
- *Stoutness.*—Willowy, flexible.
- *Diameter of shoots.*—$\frac{1}{4}$" between buds, 5/16" across buds, 5/16" through buds,
- *Flexibility.*—Flexible.
- *Internodes.*—1 11/16", long.
- *Color.*—Brown-green (23-12) on upper side, brown-green (23-14) on lower side.
- *Pubescence.*—None.
- *Texture.*—Smooth.

Lenticels:
- *Number.*—Moderate.
- *Conspicuousness.*—Summer conspicuous.
- *Shape.*—Mostly round, slightly raised.
- *Color.*—White, turning to yellowish-brown (27-9).
- *Distribution.*—Scattered.
- *Size.*—Small to medium, indistinct.

Leaves:
- *Size.*—Medium, length $2\frac{7}{8}$", breadth 1 13/16".
- *Shape.*—Broad-ovate, definite upward fold.
- *Base.*—Acute to cuneate, attenuated.
- *Apex.*—Acute, often twisted.
- *Serrations.*—Finely-Serrate.
- *Surface.*—Flat, shiny, few hairs along veins and midrib.
- *Margin.*—Tending to turn up.
- *Pose in relation to stem.*—Erect.
- *Color.*—Green (21-14) on upper surface, green (21-10) on lower surface.
- *Pubescence.*—Few hairs mostly along veins and midrib on upper surface, none on lower surface.
- *Texture.*—Pliant, smooth.
- *Color of tips of shoots.*—Pale yellowish-green (24-8) when still actively growing.

Petiole:
- *Pubescence.*—Slight on upper surface, none on lower surface.
- *Shape.*—Slender, thin, slightly channeled.
- *Length.*—Medium, 15/16".
- *Color.*—Green with reddish cast (22-10).
- *Pose.*—Erect.
- *Glands.*—None.

Stiples (not always present):
- *Size.*—Very small, narrow.
- *Margin.*—Smooth.
- *Shape.*—Medium to short, narrow, slender.
- *Length.*—$\frac{1}{4}$".
- *Color.*—Light-green (21-11).
- *Pose.*—Slightly erect.

Buds:
- *Size.*—Small to medium.

*Shape.*—Conical.

*Color.*—Brown, waxy.

*Pubescence.*—None.

*Pose.*—Somewhat appressed.

FLOWER AND FRUIT CHARACTERS

Flowers:

*Size.*—$1\frac{1}{2}''$ across, showy, dense clusters.

*Color.*—White, tinged with pink.

*Pedicels.*—$\frac{7}{8}''$ long, slender, pubsecent, greenish.

Fruit (no commercial value but useful for identification):

*Size.*—2" long, 1 13/16" wide, uniform.

*Color.*—Yellow with reddish russet.

*Stem.*—$\frac{3}{4}''$ long, very thick.

*Shape.*—Oblong, obovate, pyriform, unequal sides.

GENERAL CHARACTERISTICS

Rootsuckering: Rare.

Size control potential: Pear varieties grafted to this rootstock clone are "standard" in size.

Yield efficiency: About equal to that of trees worked on Domestic Bartlett seedling rootstocks (*Pyrus communis*).

Compatability: Graft-compatible with all major commercial fruiting varieties.

Rooting: Reproduces well by hardwood cuttings, roots arise mostly at basal cut.

Root anchorage: Good, well-anchored in both the nursery and in the orchard.

Hardiness: Hardy wherever pears are grown.

Disease resistance: Highly resistant to Fireblight (*Erwinia amylovora*), tolerant of the Pear Decline mycoplasma organism, index tested and shown to be free of known pear viruses.

Pest resistance: Average resistance to common pests of pear.

Early bearing ability: Slightly more early-bearing than like trees on Domestic seedling rootstocks.

I claim:

1. A new and distinct variety of pear tree refered to by the cultivar designation Old Home × Farmingdale #282 amd substantially as herein shown and described, characterized particularly by its ability to serve as a size-controlling rootstock for grafting of pear tree cultivars to produce "standard" pear trees; further characterized by its resistance to the Fireblight disease and its tolerance of the Pear Decline disease, further characterized by its non-rootsuckering habit, its hardiness, its good root-anchorage, its good graft-compatibility with all major commercial pear varieties, its virus freedom and its ability to root easily and reproduce readily by hardwood cuttings and by other vegetative methods.

* * * * *